(12) United States Patent
Johnson et al.

(10) Patent No.: US 8,623,004 B2
(45) Date of Patent: Jan. 7, 2014

(54) METHOD FOR DETERMINING PROXIMITY RELATIVE TO A CRITICAL STRUCTURE

(75) Inventors: Kristin D. Johnson, Louisville, CO (US); Christopher A. Valentine, Boulder, CO (US); Scott F. Alexander, Westminster, CO (US); Ronald J. Podhajsky, Boulder, CO (US)

(73) Assignee: Covidien LP, Mansfield, MA (US)

( * ) Notice: Subject to any disclaimer, the term of this patent is extended or adjusted under 35 U.S.C. 154(b) by 934 days.

(21) Appl. No.: 12/720,881

(22) Filed: Mar. 10, 2010

(65) Prior Publication Data

US 2011/0224543 A1    Sep. 15, 2011

(51) Int. Cl.
*A61B 18/18* (2006.01)

(52) U.S. Cl.
USPC .............................................. 606/32; 606/34

(58) Field of Classification Search
USPC ............................................ 606/32, 34, 42
See application file for complete search history.

(56) References Cited

U.S. PATENT DOCUMENTS

| | | | |
|---|---|---|---|
| 4,543,959 A | 10/1985 | Sepponen | |
| 5,080,104 A * | 1/1992 | Marks et al. | 600/461 |
| 5,762,609 A | 6/1998 | Benaron | |
| 5,800,350 A | 9/1998 | Coppleson et al. | |
| 5,928,158 A * | 7/1999 | Aristides | 600/547 |
| 5,928,159 A * | 7/1999 | Eggers et al. | 600/547 |
| 6,109,268 A | 8/2000 | Thapliyal | |
| 6,241,725 B1 | 6/2001 | Cosman | |
| 6,264,653 B1 * | 7/2001 | Falwell | 606/41 |
| 6,355,032 B1 * | 3/2002 | Hovda et al. | 606/32 |
| 6,428,537 B1 | 8/2002 | Swanson et al. | |
| 6,466,817 B1 * | 10/2002 | Kaula et al. | 600/546 |
| 6,546,270 B1 | 4/2003 | Goldin et al. | |
| 6,569,160 B1 | 5/2003 | Goldin et al. | |
| 6,760,616 B2 * | 7/2004 | Hoey et al. | 600/547 |
| 7,089,045 B2 | 8/2006 | Fuimaono et al. | |
| 7,099,712 B2 | 8/2006 | Fuimaono et al. | |
| 7,155,270 B2 | 12/2006 | Solis et al. | |
| 7,207,989 B2 | 4/2007 | Pike, Jr. et al. | |
| 7,228,164 B2 | 6/2007 | Fuimaono et al. | |
| 7,257,434 B2 | 8/2007 | Fuimaono et al. | |
| 7,257,435 B2 | 8/2007 | Plaza | |
| 7,302,285 B2 | 11/2007 | Fuimaono et al. | |
| 7,819,860 B2 * | 10/2010 | Wittenberger et al. | 606/23 |
| 2003/0045798 A1 | 3/2003 | Hular et al. | |

(Continued)

FOREIGN PATENT DOCUMENTS

| | | |
|---|---|---|
| EP | 1181895 | 2/2002 |
| WO | WO 2006042117 | 4/2006 |

OTHER PUBLICATIONS

European Search Report for European Application No. 11157632 dated Aug. 8, 2011.

*Primary Examiner* — Linda Dvorak
*Assistant Examiner* — Jocelyn D Ram

(57) ABSTRACT

A system for determining proximity of a surgical device relative to an anatomical structure includes at least one surgical device having a sensor assembly operably coupled to a processing unit and configured to transmit at least one electrical signal generated by the processing unit through a target anatomical structure to elicit a measurable response from the target anatomical structure. The processing unit is configured to calculate a signature property value of the target anatomical structure based on the measurable response. The processing unit is configured to identify the target anatomical structure based on a comparison between the signature property value and at least one other signature property.

8 Claims, 8 Drawing Sheets

(56) References Cited

U.S. PATENT DOCUMENTS

| | | |
|---|---|---|
| 2005/0027199 A1 | 2/2005 | Clarke |
| 2006/0106375 A1 | 5/2006 | Werneth et al. |
| 2006/0241577 A1* | 10/2006 | Balbierz et al. ................. 606/32 |
| 2007/0016097 A1* | 1/2007 | Farquhar et al. .............. 600/546 |
| 2007/0106289 A1* | 5/2007 | O'Sullivan ...................... 606/41 |
| 2007/0156128 A1 | 7/2007 | Jimenez |
| 2007/0179491 A1* | 8/2007 | Kratoska et al. ................. 606/32 |
| 2007/0248254 A1 | 10/2007 | Mysore Siddu et al. |
| 2008/0281313 A1* | 11/2008 | Fagin et al. ..................... 606/34 |
| 2009/0163904 A1* | 6/2009 | Miller et al. .................... 606/33 |
| 2009/0267773 A1 | 10/2009 | Markowitz et al. |
| 2009/0275827 A1 | 11/2009 | Aiken |
| 2011/0270121 A1* | 11/2011 | Johnson et al. ............... 600/554 |
| 2011/0275952 A1* | 11/2011 | Johnson et al. ............... 600/547 |

* cited by examiner

METHOD FOR DETERMINING PROXIMITY RELATIVE TO A CRITICAL STRUCTURE

BACKGROUND

1. Technical Field

The present disclosure relates to open or endoscopic surgical instruments and methods for treating tissue. More particularly, the present disclosure relates to a system and method for determining proximity of a surgical device relative to critical anatomical structures utilizing signature properties values of such structures.

2. Background of Related Art

A hemostat or forceps is a simple plier-like tool that uses mechanical action between its jaws to constrict vessels and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue.

Over the last several decades, more and more surgeons are complementing traditional open methods of gaining access to vital organs and body cavities with endoscopes and endoscopic instruments that access organs through small puncture-like incisions. Endoscopic instruments are inserted into the patient through a cannula, or port, that has been made with a trocar. Typical sizes for cannulas range from three millimeters to twelve millimeters. Smaller cannulas are usually preferred, which, as can be appreciated, ultimately presents a design challenge to instrument manufacturers who must find ways to make surgical instruments that fit through the cannulas.

As mentioned above, by utilizing an electrosurgical instrument, a surgeon can either cauterize, coagulate/desiccate and/or simply reduce or slow bleeding, by controlling the intensity, frequency and duration of the electrosurgical energy applied through the jaw members to the tissue. The electrode of each jaw member is charged to a different electric potential such that when the jaw members grasp tissue, electrical energy can be selectively transferred through the tissue.

Bipolar electrosurgical instruments are known in the art, as are other electrosurgical instruments. Commonly-owned U.S. Patent Application Publication No. 2007-0062017, discloses a bipolar electrosurgical instrument. Conventional bipolar electrosurgical instruments may include a cutting blade, fluid applicator, stapling mechanism or other like feature, in various combinations.

Different types of anatomical structures, i.e. vessels, ducts, organs, may require different energy delivery configurations to effect proper treatment. While a specific energy delivery configuration may be adequate for treating an artery or vein, the same energy delivery configuration may not be suitable for treating a duct. Although in certain scenarios the identity of an anatomical structure being treated is either known or visually apparent, there may be instances where a surgeon is unable to visually determine the anatomical structure being treated. Treating non-target structures with an energy configuration configured for a target type structure may cause damage to the non-target structure and/or result in failure to effect proper treatment.

During certain procedures, surgeons must identify critical anatomical structures such as large vasculature or urinary or bile ducts. These structures typically need to be avoided or ligated during a procedure, thus requiring a high degree of confidence when identifying such structures.

One complication during laparoscopic procedures in particular, is inadvertently injuring nearby critical anatomical structures due to quick or abrupt movement of instruments within the surgical site, poor visibility, lack of tactile response, confusion of the anatomy from patient to patient, or inadequate control of the instrumentation being utilized to perform the procedure. For example, when performing a laparoscopic cholecystectomy to remove the gallbladder, a critical aspect of the procedure is the identification of the common bile duct. Injuries to the common bile duct may result in significant health risks. For example, despite the use of increased dissection and cholangiograms to identify critical structures such as the common bile duct, a common bile duct injury rate of 0.5% to 1.4% has been reported.

Traditional methods for identifying anatomical structures within the body are based on sensing physical characteristics or physiological attributes of body tissue, and then distinguishing normal from abnormal states from changes in the characteristic or attribute. For example X-ray techniques measure tissue physical density, ultrasound measures acoustic density, and thermal sensing techniques measures differences in tissue heat.

Signature properties of anatomical structures such as electrical conductivity, impedance, thermal conductivity, permittivity, and capacitance may be measured and compared to known data to distinguish anatomical structures from other anatomical structures and/or known data. If these signature properties can be properly elicited from a target anatomical structure, measureable values that correspond to these elicited properties may be calculated and compared to known values for purposes of identifying the target anatomical structure.

SUMMARY

According to an embodiment of the present disclosure, a system for determining proximity of a surgical device relative to an anatomical structure includes at least one surgical device having a sensor assembly operably coupled to a processing unit. The sensor assembly is configured to transmit at least one electrical signal generated by the processing unit through a target anatomical structure to elicit a measurable response from the target anatomical structure. The processing unit is configured to calculate a signature property value of the target anatomical structure based on the measurable response. The processing unit is configured to determine proximity of the at least one surgical device relative to the target anatomical structure based on a comparison between the signature property value and at least one other signature property.

According to another embodiment of the present disclosure, a method for determining proximity of a surgical device relative to an anatomical structure includes the steps of placing at least one surgical device having a sensor assembly disposed thereon relative to a target anatomical structure and transmitting at least one electrical signal from the sensor assembly through the target anatomical structure to elicit a measurable response from the anatomical structure. The method also includes the steps of calculating one or more signature properties of the target anatomical structure based on the measureable response and comparing values of the one or more measured signature properties to at least one other measured signature property. The method also includes the step of determining proximity of the at least one surgical device relative to the target anatomical structure based on the comparison between the one or more measured signature properties and at least one other measured signature property.

According to another embodiment of the present disclosure, a method for identifying an anatomical structure includes the steps of placing at least one surgical device having a sensor assembly disposed thereon relative to a target anatomical structure and transmitting at least one electrical signal from the sensor assembly through the target anatomical structure to elicit a measurable response from the anatomical structure. The method also includes the steps of calculating one or more signature properties of the target anatomical structure based on the measureable response and comparing values of the one or more measured signature properties to at least one other measured signature property. The method also includes the steps of identifying the target anatomical structure based on the comparison between the one or more measured signature properties and at least one other measured signature property and selectively applying energy to the target anatomical structure based on the identifying step.

BRIEF DESCRIPTION OF THE DRAWINGS

Various embodiments of the subject instrument are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

An electrosurgical generator according to the present disclosure can perform monopolar and bipolar electrosurgical procedures, including anatomical tissue ligation procedures. The generator may include a plurality of outputs for interfacing with various bipolar and monopolar electrosurgical instruments (e.g., laparoscopic electrodes, return electrodes, electrosurgical forceps, footswitches, etc.). Further, the generator includes electronic circuitry configured to generate electrosurgical energy (e.g., RF, microwave, etc.) specifically suited for various electrosurgical modes (e.g., cut, coagulate (fulgurate), desiccate, etc.) and procedures (e.g., ablation, vessel sealing, etc.).

The present disclosure generally relates to a system for identifying a target anatomical structure such as, for example, a duct, organ, vasculature, vessel, and the like. The system transmits one or more electrical signals from a sensor assembly disposed on one or more surgical instruments through the target structure to elicit a measureable response therefrom. Based on the response, the system calculates one or more signature property values of the target structure and compares these values to known signature property values of various structures and/or to other target structures from which a measurable response has been elicited. Based on the comparison, the system identifies the target anatomical structure and alerts a user of the system as to the distance of the target structure relative to the sensor assembly and/or the identity of the target structure (e.g., duct vs. large artery or background connective tissue).

Figure 1A:
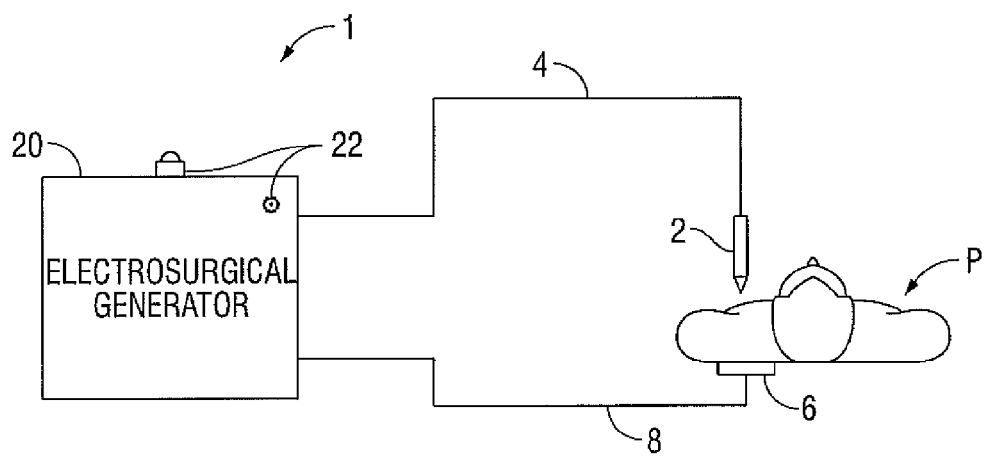
FIG. 1A is a schematic block diagram of a monopolar electrosurgical system in accordance with an embodiment of the present disclosure.

FIG. 1A is a schematic illustration of a monopolar electrosurgical system 1 according to one embodiment of the present disclosure. The system 1 includes an electrosurgical instrument 2 having one or more electrodes for treating tissue of a patient P. The instrument 2 is a monopolar type instrument (e.g., electrosurgical cutting probe, ablation electrode(s), etc.) including one or more active electrodes. Electrosurgical energy is supplied to the instrument 2 by a generator 20 via a supply line 4 that is connected to an active terminal 30 (FIG. 2) of the generator 20, allowing the instrument 2 to coagulate, seal, cut, ablate, and/or otherwise treat tissue. The electrosurgical energy is returned to the generator 20 through a return electrode 6 via a return line 8 at a return terminal 32 (FIG. 2) of the generator 20.

Figure 1B:
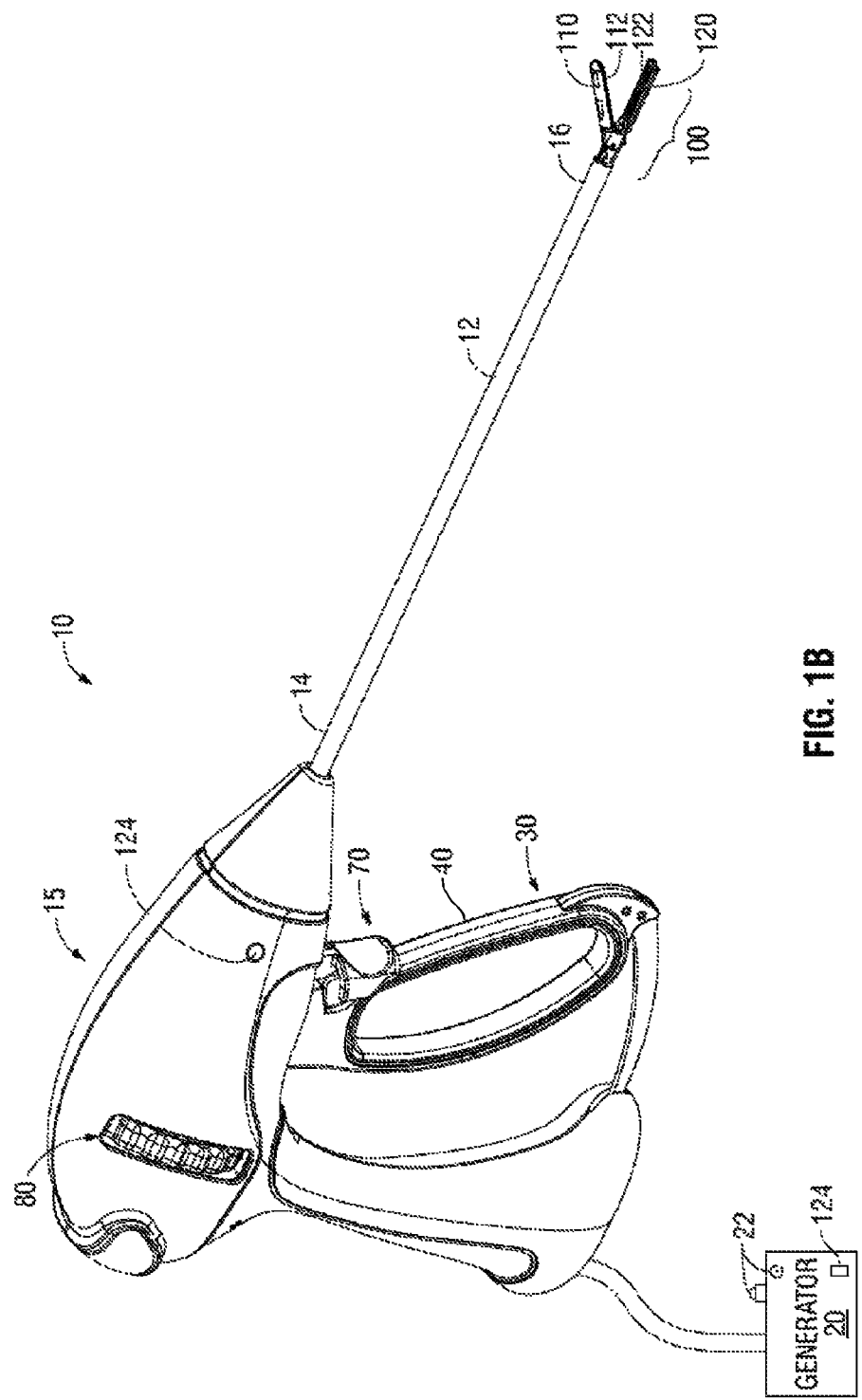
FIG. 1B is a schematic block diagram of a bipolar electrosurgical system in accordance with an embodiment of the present disclosure.

Turning now to FIG. 1B, an instrument generally identified as bipolar forceps 10 is for use with various surgical procedures and includes a housing 15, a handle assembly 30, a rotating assembly 80, a trigger assembly 70, and an end effector assembly 100 that mutually cooperate to grasp, seal, and divide tubular vessels and vascular tissues. Forceps 10 includes a shaft 12 that has a distal end 16 dimensioned to mechanically engage the end effector assembly 100 and a proximal end 14 that mechanically engages the housing 15. The end effector assembly 100 includes opposing jaw members 110 and 120 that cooperate to effectively grasp tissue for sealing purposes. With this purpose in mind, jaw members 110 and 120 include active electrodes 112 and 122 disposed thereon in a bipolar configuration. Active electrodes 112, 122 are operably coupled to generator 20 and are configured to selectively apply electrosurgical energy supplied from the generator 20 to tissue grasped between the jaw members 110, 120. The end effector assembly 100 may be designed as a unilateral assembly, e.g., jaw member 120 is fixed relative to the shaft 12 and jaw member 110 pivots relative to jaw member 120 to grasp tissue, or as a bilateral assembly, e.g., jaw members 110 and 120 pivot relative to each other to grasp tissue.

Examples of forceps are shown and described in commonly-owned U.S. application Ser. No. 10/369,894 entitled "VESSEL SEALER AND DIVIDER AND METHOD MANUFACTURING SAME" and commonly-owned U.S. application Ser. No. 10/460,926 (now U.S. Pat. No. 7,156,846) entitled "VESSEL SEALER AND DIVIDER FOR USE WITH SMALL TROCARS AND CANNULAS".

Although the following disclosure focuses predominately on discussion of electrosurgical instruments for use in connection with endoscopic surgical procedures, open type instruments are also contemplated for use in connection with traditional open surgical procedures. Additionally and as discussed in greater detail below, the aspects of the present disclosure may be incorporated into any suitable electrosurgical instrument (e.g., instrument 2, forceps 10) or any suitable non-electrosurgical instrument (e.g., probes, graspers, prods, clamps, grips, forceps, pliers, cutters, electrocautery devices, etc.).

Figure 2:
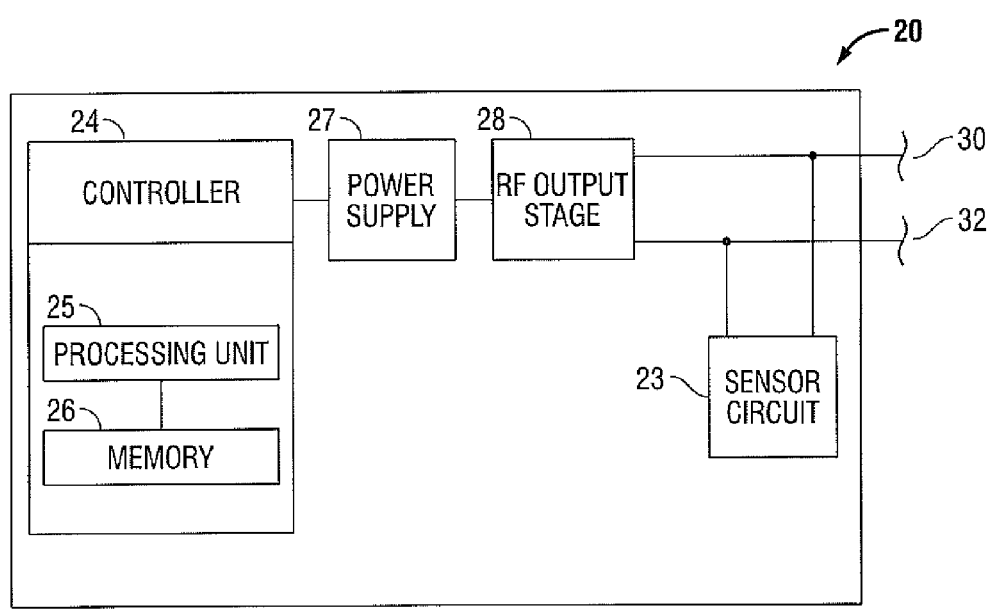
FIG. 2 is a schematic block diagram of a generator in accordance with an embodiment of the present disclosure.

FIG. 2 shows a schematic block diagram of the generator 20 having a controller 24, a high voltage DC power supply 27 ("HVPS"), a sensor module 23, and an energy output stage 28 configured to output electrosurgical energy (e.g., microwave, RF, etc.) from generator 20. The HVPS 27 is connected to a conventional AC source (e.g., electrical wall outlet) and provides high voltage DC power to the energy output stage 28, which then converts high voltage DC power into electrosurgical energy for delivery to the active electrode(s) of an electrosurgical instrument (e.g., instrument 2, forceps 10, etc.) via the active terminal 30. In certain embodiments (FIGS. 1A and 1B), the electrosurgical energy is returned to the generator 20 via the return terminal 32.

The generator 20 may include a plurality of connectors to accommodate various types of electrosurgical instruments (e.g., instrument 2, electrosurgical forceps 10, etc.). Further, the generator 20 may operate in monopolar or bipolar modes by including a switching mechanism (e.g., relays) to switch the supply of electrosurgical energy between the connectors, such that, for instance, when the monopolar type instrument 2 is connected to the generator 20, only the monopolar plug receives electrosurgical energy.

The controller 24 includes a processing unit 25 operably connected to a memory 26, which may be volatile type memory (e.g., RAM) and/or non-volatile type memory (e.g., flash media, disk media, etc.). The processing unit 25 may be any logic processor or analog circuitry (e.g., microprocessor, control circuit, etc.) adapted to perform the calculations discussed in the present disclosure. The processing unit 25 includes an output port that is operably connected to the HVPS 27 and/or the energy output stage 28 allowing the processing unit 25 to control the output of the generator 20 according to either open and/or closed control loop schemes.

A closed loop control scheme generally includes a feedback control loop wherein the sensor module 23 provides feedback to the controller 24 (e.g., information obtained from one or more sensing mechanisms that sense various tissue parameters such as tissue impedance, tissue temperature, tissue conductivity, tissue permittivity, output current and/or voltage, etc.). The controller 24 then signals the power supply 27, which then adjusts the DC power supplied to the RF output stage 28, accordingly. The controller 24 also receives input signals from the input controls of the generator 20 and/or instrument 2 or forceps 10. The controller 24 utilizes the input signals to adjust the power output of the generator 20 and/or instructs the generator 20 to perform other control functions. In some embodiments, the generator 20 may utilize audio-based and/or a video-based display to inform the user of the sensed tissue parameters in the field of view of the one or more sensing mechanisms.

The processing unit 25 is capable of executing software instructions for processing data received by the sensor module 23, and for outputting control signals to the generator 20 or other suitable operating room devices (e.g., camera monitor, video display, audio output, etc.), accordingly. The software instructions, which are executable by the controller 24, are stored in the memory 26 of the controller 24. The controller 24 may include analog and/or logic circuitry for processing the sensed values and determining the control signals that are sent to the generator 20, rather than, or in combination with, the processing unit 25.

In some embodiments, generator 20 and processing unit 25 may be separate stand-alone units operably connected to each other (not shown) or processing unit 25 may be incorporated within generator 20, as shown in FIG. 2. In some embodiments, processing unit 25 may be incorporated within the surgical device being used during a procedure (e.g., instrument 2, forceps 10). In this scenario, the signal-to-noise ratio of signals transmitted to and from processing unit 25 may be improved since the signals may experience a decrease in losses caused by travel through relatively long lengths of cable. For ease of disclosure, generator 20 is described as incorporating processing unit 25 and processing unit 25 is, in turn, described as being incorporated within generator 20.

Figure 3:
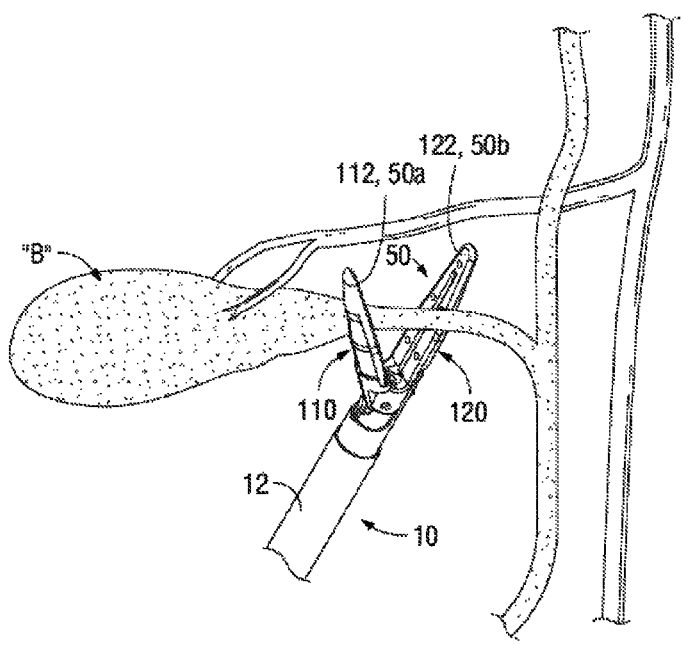
FIG. 3 is a perspective view of a bipolar forceps disposed relative to a gallbladder region of a patient in accordance with an embodiment of the present disclosure.
Figure 4A:
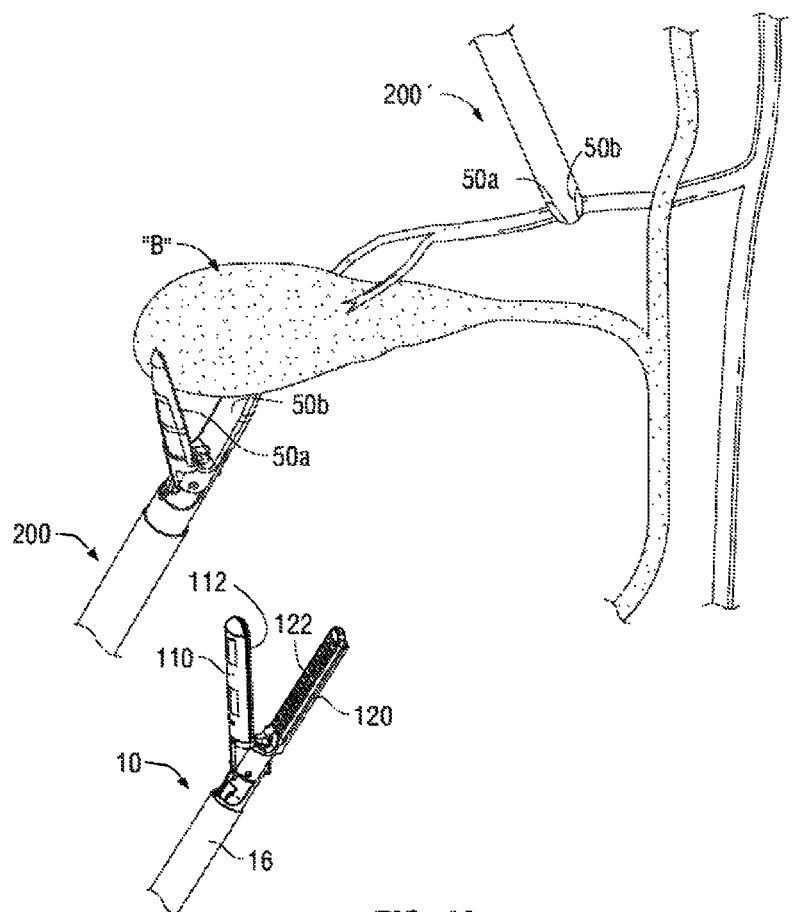
FIG. 4A is a perspective view of a bipolar forceps, a grasper, and a dissector or probe disposed relative to a gallbladder region of a patient in accordance with another embodiment of the present disclosure.
Figure 4B:
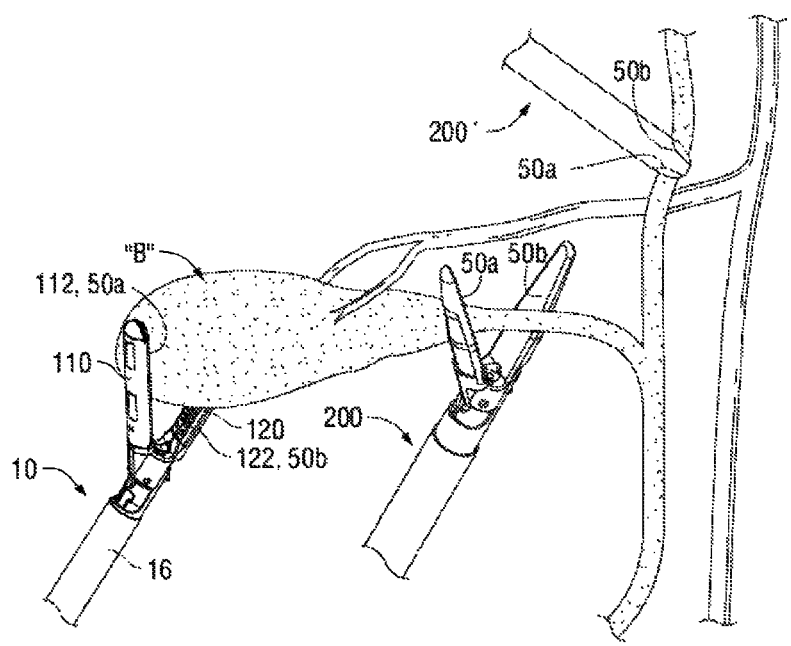
FIG. 4B is a perspective view of a of a bipolar forceps, a grasper, and a dissector or probe disposed relative to a gallbladder region of a patient in accordance with another embodiment of the present disclosure.
Figure 5:
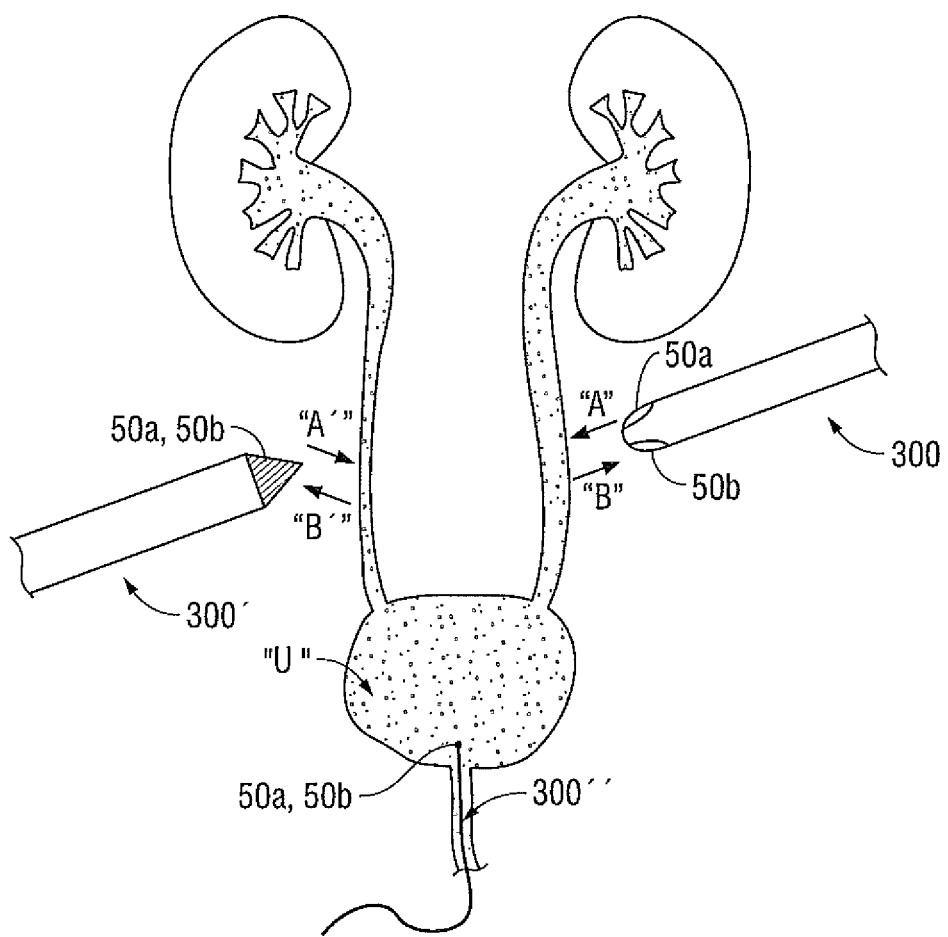
FIG. 5 is a perspective view of probe-type devices and a catheter-type device disposed relative to a bladder and kidney region of a patient in accordance with another embodiment of the present disclosure.

Processing unit 25 is operably connected to an electrode or sensor assembly 50 (FIG. 3). As will be discussed in further detail below, sensor assembly 50 includes one or more transmitting electrodes 50a and one or more receiving electrodes 50b and may be mounted on one or more suitable electrosurgical instruments such as, for example, monopolar instrument 2 or forceps 10, or on one or more suitable non-electrosurgical instruments such as, for example, a grasper 200 or a dissector or probe 200', as shown in FIGS. 4A and 4B, and probe-type instruments 300 and 300' and a catheter 300", as shown in FIG. 5. In this scenario, the generator 20 may include a plurality of connectors to accommodate non-electrosurgical instruments such that a sensor assembly 50 mounted to such an instrument may communicate with the generator and/or the processing unit 25 for purposes of identifying target anatomical structures.

Sensor assembly 50 is configured to sense and/or measure various properties of anatomical structures and/or tissue such as, without limitation, electrical conductivity, thermal conductivity, fluid flow, temperature, capacitance, permittivity, voltage, current, optical-based information, etc. With these purposes in mind, sensor assembly 50 may be embodied as an impedance sensor, a temperature sensor, an optical sensor, a fluid flow sensor, a capacitance sensor, a permittivity sensor, a voltage sensor, a current sensor, a pressure sensor, or a combination of any two or more thereof.

In some embodiments, sensor assembly 50 may be mounted on a distal end of one or more electrosurgical and/or non-electrosurgical instruments such that the sensor assembly 50 may be used to sense ahead to the area that the user is moving the treatment device (e.g., instrument 2, forceps 10) to prevent incidental contact between surgical instruments and critical anatomical structures, as discussed hereinabove. In this embodiment, one or more receiving electrodes 50b may be disposed on the instrument the user is moving toward a desired tissue site and one or more transmitting electrodes 50a may be disposed on a second instrument placed relative to the desired tissue site (e.g., during a dissection procedure).

In some embodiments, sensor assembly 50 may be disposed on or split between two separate instruments such that either the transmitting electrode 50a or the receiving electrode 50b is disposed on a first instrument and the other electrode 50a, 50b is disposed on a second instrument. This scenario is shown by way of example in FIG. 5. For example, FIG. 5 shows catheter 300" disposed through a bladder and partially into the right ureter of a patient and probe 300' in the proximity of the exterior of said right ureter. One of catheter 300" and probe 300' includes a transmitting electrode 50a disposed thereon and the other instrument includes a receiving electrode 50b disposed thereon to operate in cooperation with the transmitting electrode 50a. As indicated by arrows "A'" and "B'" in FIG. 5, transmitting electrode 50a may transmit electrical signals directionally or radially outward from within an anatomical structure (e.g., catheter 300") or toward an anatomical structure (e.g., instrument 300'), such that the transmitted electrical signals will solicit a response from the target anatomical structure that may be processed by the processing unit 25. In this manner, the processing unit 25 may determine the identity of the target anatomical structure, as discussed hereinabove.

In certain embodiments, the transmitting electrode 50a and the receiving electrode 50b may be substituted by the active electrodes (e.g., 112, 122) of an electrosurgical instrument utilized in the procedure such as forceps 10, shown by way of example in FIG. 3. Either of electrodes 112, 122 may be the transmitting electrode 50a and the other electrode 112, 122 may be the receiving electrode 50b. In this manner, active electrodes 112, 122 may be utilized to sense tissue of the target critical structure so that the user may identify the target critical structure prior to the application of treatment energy thereto and avoid inadvertent treatment to surrounding critical anatomical structures. In one embodiment, each of the active electrodes 112, 122 may be split into more than one active electrode. This configuration allows smaller predefined surface areas that are configured to source and/or receive the electrical signal through tissue and, thus, may be more suitable in larger jaw instruments. Additionally or alternatively, an insulative material (not shown) may be disposed between the jaw members 110, 120 to limit the surface area of the active electrodes 112, 122. In a grasping or bipolar type embodiment, the pressure applied to tissue grasped between the jaw members 110, 120 may be optimized to provide the most accurate information or tissue property data. For example, if clamped too hard on a duct, the contents within the duct may have limited contribution to the electrical signature of the duct (e.g., conductivity) or no contribution to the electrical signature of the duct. If the pressure is too light or not controlled, the electrical signature measurements of the duct may be less repeatable or less accurate.

Although the following discussion will relate to a two-electrode method of measuring signature properties of anatomical structures, other methods of measuring signature properties of anatomical structures have been contemplated by the present disclosure. In the two-electrode method, two electrodes are placed in contact with, penetrate into, or are placed in proximity with the tissue and/or the anatomical structure to be tested. In one procedure utilizing the two-electrode method, a sinusoidal voltage is applied through an anatomical structure across two electrodes and the resultant sinusoidal current flow through the structure is measured. The magnitude of the structure impedance may be determined as the ratio of the root-mean-square (RMS) voltage and the current values. The phase angle of the impedance may be determined as the delay in radians of the peak sinusoidal current with respect to the peak sinusoidal voltage. By comparing the resulting impedance values with known values for various anatomical structures, the anatomical structure may be identified. Embodiments of the present disclosure are not limited to the methods of determining the signature properties disclosed herein. Any suitable method for measuring signature properties of anatomical structures, whether electrical, thermal, optical, or the like, may be incorporated into the embodiments of the present disclosure.

Briefly, a predetermined energy signal is periodically produced by the processing unit 20 and applied to the target anatomical structure (e.g., vasculature, duct, vessel, organ, etc.) through the transmitting electrode 50a, 112 and received by the receiving electrode 50b, 122. The resultant response of the target structure to the electrical signal is processed by the processing unit 25 and is then measured and converted into a value of a particular signature property by which an anatomical structure may be identified. For example, and without limitation, electrical conductivity, thermal conductivity, hydraulic conductivity, impedance, capacitance, and permittivity are all signature properties by which an anatomical structure may be identified. These signature properties as measured may include or capture the contents (e.g., fluids) of the anatomical structure. That is, anatomical structures such as vessels or ducts may include fluid content flowing therethrough such as bile, blood, urine, saliva, mucus, water, feces, digestive enzymes, and the like, that directly affect the response elicited from the target anatomical structure and, thus, the resulting calculated signature properties. By capturing the content of an anatomical structure in the signature property measurement, such anatomical structures may better be distinguished from surrounding or background tissue as well as surrounding or attached anatomical structures. By comparing such signature property measurements with known signature property measurements of various anatomical structures, processing unit 25 may determine, in real-time, the identity of an anatomical structure being sensed by the sensor assembly 50 based on the comparison between sensed and known signature property measurements.

In other embodiments, assessments of anatomical structure identification may be made based on the differences between signature properties of more than one anatomical structure being sensed by the sensor assembly 50. In this scenario, shown by way of example in FIGS. 4A and 4B, more than one instrument (e.g., forceps 10, grasper 200, instrument 2, dissector/probe 200') may be used during a procedure, each of which includes a sensor assembly 50 configured to elicit a response from a target anatomical structure such that the processing unit 25 may calculate a signature property of such target structure. Based on the differences between the calculated signature properties of the different anatomical structures (e.g., cystic duct vs. cystic artery), as determined by the processing unit 25, the user is alerted by the processing unit 25 and/or generator 20 as to the identity of such target structures. The user may manually make an assessment based on data presented by the processing device 25 and/or may automatically be alerted as to the identity of sensed anatomical structures, e.g., via a visual display or user interface disposed on the generator 20 and/or processing unit 25. Alternatively or additionally, sensor assembly 50 may be configured to optically sense the target anatomical structure such that the user is able to view the target structure (e.g., via the display on the generator 20).

In some embodiments, sensor assembly 50 may be configured to sense signature thermal properties of a target anatomical structure. In this scenario, a contrast agent or fluid having a different temperature than the body of the patient such as, for example without limitation, cold saline or Iodine, may be injected into the body of a patient to better distinguish target anatomical structures, for example, by affecting the thermal conductivity of a target anatomical structure. For example, cold saline flowing through the ureter of a patient will operate to distinguish the ureter from surrounding connective tissues.

In certain scenarios, it may be necessary to differentiate anatomical structures utilizing more than one modality and/or more than one signature property of such structures. For example, the signature electrical properties of veins may be similar to that of arteries, thereby making differentiating such structures from each other difficult utilizing only signature electrical properties. Through use of the various embodiments of the present disclosure, electrical and/or other signature tissue properties (e.g., thermal properties) may be sensed and used in combination with other sensed properties such as, for example, pressure within the vein or artery and/or optical data of the vein or artery, to more easily differentiate one from the other.

In operation of one embodiment of the present disclosure, sensor assembly 50 is placed in contact with or in proximity to the target anatomical structure to be identified. Processing unit 25 produces an electric signal that is directed into the target structure through transmitting electrode 50a. Processing unit 25 may be configured to continuously or periodically produce a signal, or instead the instrument being utilized (e.g., bipolar forceps 10) may include a button or lever 124 mounted on housing 15 and/or generator 20 (FIG. 1B) for activating processing unit 25. As discussed above, depending on the application, the electric signal may be of a specific frequency or range of frequencies and of any configuration. The respective portion of the target structure disposed between transmitting electrode 50a and receiving electrode 50b (e.g., tissue and fluid contents within the structure) functions to complete a circuit path therebetween. In this manner, conductive anatomical structures and/or their conductive content (e.g., bile, urine, etc.) may be utilized to transmit the electric signal a longer distance between the transmitting and receiving electrodes 50a and 50b such that transmitting and receiving electrodes 50a and 50b need not be in close proximity to each other to complete a circuit therebetween. These portions of the target structure produce characteristic responses based on the signals delivered to electrode 50a by processing unit 25. The resulting response is acquired by receiving electrode 50b. Based on the response, the processing unit 25 calculates signature property values of the target structure. By comparing the signature property values of the target structure with signature property values of other target structures and/or with known values of various structures, the identity of the target structure may be identified.

Once the target anatomical structure has been identified, a treatment device such as bipolar forceps 10 may operate as a conventional bipolar vessel sealer. The energy delivery configuration of generator 20 may be adjusted in accordance with the identified anatomical structure being treated. The closure pressure of the opposing jaw members 110, 120 may also be adjusted in view of the anatomical structure being sealed.

The electrical current produced by the processing unit 25 may vary depending on the type of tissue and/or the anatomical structure (e.g., duct, vasculature, vessel, organ, etc.) being identified. Processing unit 25 is configured to produce AC and/or DC current. Processing unit 25 may be configured to generate an electrical signal having a frequency ranging from RF (100 kHz) upwards of microwaves (low MHz to GHz). Depending on the application, processing unit 25 may produce a signal of constant frequency, a cascaded pulse interrogation signal (e.g., a cosign shaped pulse), or may instead perform a frequency sweep or amplitude sweep.

More than one sensor assembly 50 may be connected to the processing unit 25. In this manner, the one or more sensor assemblies 50 of a particular instrument may include different electrode configurations depending on the anatomical structure and/or signal frequency being tested. Processing unit 25 may include any suitable methods of increasing the accuracy and consistency of the signature tissue property measurements, e.g., filters and multi-frequency readings.

Processing unit 25 may operate in a number of modes. Processing unit 25 may be configured to alert a user when sensor assembly 50 has contacted a specific anatomical structure (e.g., vasculature, duct, vessel, tissue, organ, etc.). In this manner, a user would set processing unit 25 to scan for a particular signature property (e.g., electrical conductivity, thermal conductivity, capacitance, impedance, etc.). Processing unit 25 produces an electrical signal configured to best identify the signature tissue property. The electrical signal produced by processing unit 25 may be manually determined by the user or may instead be automatically determined by processing unit 25. The electrical signal produced may include a specific frequency or range of frequencies and/or may include a specific signal configuration. Sensor assembly 50 may be placed in contact over a portion of tissue or in close proximity thereto. As sensor assembly 50 contacts or approaches tissue of the target type, as determined by processing unit 25, processing unit 25 may alert the user. The alert may be audio and/or visual. With this purpose in mind, an audio and/or visual indicator 22 (FIGS. 1A and 1B) may be included in/on the generator 20 and/or the instrument utilized in the procedure (not explicitly shown).

One example procedure where identification of target and surrounding critical anatomical structures is important is laparoscopic cholecystectomies to remove a gallbladder from a patient. By way of example, FIGS. 3, 4A, 4B, and 6 show a general rendering of the gallbladder region of a patient to illustrate the presenting of electrosurgical and/or non-electrosurgical instruments relative to such region. In this procedure, a surgeon removes the gallbladder from the cystic duct and occludes the cystic duct to prevent bile leaking from the common bile duct. Therefore, the cystic duct must be correctly identified by the surgeon so that the cystic duct, rather than the common bile duct, receives treatment (e.g., RF energy, microwave energy, excision, resection, occlusion, ligating, etc.). Other critical structures, such as the cystic artery and hepatic artery are in close proximity to the cystic duct and common bile duct and must be correctly identified by the surgeon so as to avoid treating or otherwise inadvertently injuring such critical structures.

Another procedure where identification of target and surrounding anatomical structures is important is an ureterostomy. By way of example, FIG. 5 shows a general rendering of a bladder and kidney region of a patient to illustrate the presenting of electrosurgical and/or non-electrosurgical instruments relative thereto. In this procedure, the surgeon detaches one or both ureters disposed between the kidneys and the bladder. Therefore, the ureter(s) must be correctly identified by the surgeon so that the ureter(s), rather than the bladder or kidneys, receives treatment. During other procedures, such as gynecological and colorectal procedures, nearby critical structures such as the ureter(s) are to be avoided and, thus, correct identification thereof is important so that the surgeon is able to avoid treatment of the ureter(s) and/or incidental contact between a surgical device and the ureter(s).

Turning now to FIGS. 3-6, various embodiments of electrosurgical and non-electrosurgical instruments that are utilized in conjunction with one or more sensor assemblies 50 are shown and include, without limitation, monopolar instrument 2, bipolar forceps 10, grasper 200, dissectors/probes 200', 300, 300', and catheter 300". Referring initially to FIG. 3, electrodes 112, 122 of bipolar forceps 10 are embodied as the active and receiving electrodes 50a, 50b of sensor assembly 50, respectively. Forceps 10 is shown with a target anatomical structure (e.g., cystic duct) disposed between jaw members 110, 120 while in an open position. In this scenario, while grasping (or prior to grasping) the target anatomical structure with forceps 10, the processing unit 25 transmits the electrical signal from the transmitting electrode 112, 50a through the target anatomical structure and/or the contents (e.g., bile) of the target anatomical structure (referenced generally as "B") to the receiving electrode 122, 50b to elicit a response from the target structure. Once the target anatomical structure is identified by the processing unit 25, by methods described hereinabove, the user is alerted by the audio/visual indicator 22 as to the identity of the target structure. If the identity of the target anatomical structure is revealed to be the target structure designated for treatment, the user may either grasp the target structure between jaw members 110, 120, if such structure was not already grasped between jaw members 110, 120, and selectively apply electrosurgical energy from the generator 20 to the structure. If the identity of the target structure is revealed to be a critical structure not in need of treatment and/or to be avoided to prevent unnecessary treatment to the patient, the user may release the target structure from the grasp of jaw member 110, 120, if necessary, and move forceps 10 away from such structure to avoid complications.

Referring now to FIG. 4A, a plurality of surgical instruments including forceps 10, a grasper 200, and a dissector or probe 200' are shown and may be used during a procedure in conjunction with a sensor assembly 50 to elicit a response from a target anatomical structure such that the processing unit 25 may calculate a signature property measurement of such target structure. More specifically, grasper 200 is shown in an open position with a target anatomical structure (e.g., gallbladder) disposed between the transmitting and receiving electrodes 50a, 50b. Dissector/probe 200' is shown positioned about a different anatomical structure (e.g., cystic artery) than grasper 200. In this scenario, prior to grasping a target anatomical structure with forceps 10, the grasper 200 and/or the dissector/probe 200' may be utilized in conjunction with processing device 25 to identify respective anatomical structures, using methods described hereinabove. For example, transmitting electrode 50a disposed on grasper 200 may be utilized to transmit an electrical signal to receiving electrode 50b (e.g., disposed on grasper 200, dissector/probe 200', or any other suitable instrument) via the conductive tissue of the gallbladder and/or the conductive content within the gallbladder (e.g., bile), referenced generally as "B", to elicit a measurable response from the gallbladder. In the illustrated embodiment, once the grasper 200 retracts the gallbladder and the dissector/probe 200' correctly identifies the cystic artery, forceps 10 may be subsequently navigated by the user away from the cystic artery and toward the cystic duct for subsequent grasping and applying of electrosurgical energy thereto. As discussed hereinabove, the identity of these anatomical structures may be based on the differences between the calculated signature properties thereof (e.g., cystic duct vs. cystic artery) and/or based on the comparison between the calculated signature properties thereof and known signature property values of various anatomical structures, as determined by the processing unit 25.

Referring now to FIG. 4B, a plurality of surgical instruments including forceps 10, grasper 200, and dissector/probe 200' are shown and may be used during a procedure in conjunction with a sensor assembly 50 to elicit a response from a target anatomical structure such that the processing unit 25 may calculate a signature property measurement of such target structure. More specifically, forceps 10 is shown grasping the gallbladder between jaw members 110, 120, grasper 200 is shown in an open position with a target anatomical structure (e.g., cystic duct) disposed between the transmitting and receiving electrodes 50a, 50b, and dissector/probe 200' is shown positioned about a different anatomical structure (e.g., common bile duct) than grasper 200 and forceps 10. In this scenario, any one or combination of forceps 10, grasper 200, and dissector/probe 200' may be utilized to source or transmit the electrical signal generated by processing unit 25 via a transmitting electrode 50a to a receiving electrode 50b disposed on any one or more of the above listed instruments utilizing anatomical structures and/or the contents (e.g., bile "B", urine "U", etc,) of such anatomical structures to complete a circuit therebetween. That is, the content (e.g., bile "B", urine "U", etc.) within the various anatomical structures (e.g., gallbladder, common bile duct, cystic duct, etc.) may operate to complete a circuit between any one or more transmitting electrodes 50a and any one or more receiving electrodes 50b of the illustrated instruments (e.g., forceps 10, grasper 200, dissector/probe 200').

The number and combination of instruments used to perform each of the methods of the various embodiments described herein are illustrative only in that any number of instruments and any combination of instruments may be incorporated to perform the methods described with respect to the illustrated embodiments of FIGS. 3, 4A, 4B, 5, and 6.

In some embodiments, forceps 10 and/or grasper 200 may include a pressure sensor (not explicitly shown) configured to sense grasping pressure applied to a target anatomical structure (e.g., via jaw members 110, 120). For example, the pressure sensor may be embodied as a two-dimensional pressure sensor pad disposed on the grasping surface(s) of grasper 200 and/or forceps 10. In this way, when a target anatomical structure is grasped by grasper 200 or forceps 10, the grasping pressure applied to the target structure may be sensed and optimized for eliciting a response therefrom using transmission of the electrical signal from processing unit 25 therethrough. More specifically, if too little pressure is applied to the target structure, the electrical signal transmitted through the structure may be too weak to elicit a response. Likewise, if too much pressure is applied to the target structure (especially relevant when applying pressure to ducts or vessels), the target structure may be occluded, thereby not allowing for the inclusion of fluid flow through the target structure when calculating signature properties thereof. In one embodiment, the pressure applied to the target structure may be optimized by initially eliciting a response in the target structure while increasing the applied pressure thereto until a step or a threshold change in conductivity is sensed. Once the step or threshold change in conductivity is sensed, pressure applied to the target structure may be decreased to allow for fluid flow through the target structure, at which time a response is again elicited from the target structure, thereby providing a relatively more reliable and repeatable measurement of signature properties of the target structure that includes the flow of fluid therethrough. Controlling pressure also ensures that anatomical structures are not inadvertently crushed between the closing jaw members (e.g., jaw members 110, 120) of a vessel sealing type instrument (e.g., forceps 10). With this purpose in mind, an initial sensing pressure may be applied to the target structure followed by a tissue sealing pressure, with the vessel sealing type instrument configured to control each of the initial sensing pressure and the sealing pressure.

The two-dimensional pressure sensor may also be used to identify tubular structures within a jaw member(s) 110, 120. The identification of a tubular structure (e.g. duct, artery, etc.) in combination with the sensed electrical properties, thermal properties, optical properties, etc. of the tissue may add additional information that better identifies the critical structure within jaw members 110, 120.

In certain embodiments, sensor assembly 50 may be disposed at the distal end of a suitable instrument (e.g., forceps 10) such that as sensor assembly 50 approaches a target anatomical structure, processing unit 20 may first identify the target structure and subsequently alert the user via audio/visual indicator 22 as to the identity of the anatomical structure being approached and/or sensed in the proximity of sensor assembly 50. This scenario is shown, by way of example, in FIG. 5. In particular, probe 300 is shown approaching a left ureter of a patient and probe 300' is shown approaching a right ureter of a patient in proximity to catheter 300''' disposed within the right ureter, as discussed hereinabove. The distance between the sensor assembly 50 and a target anatomical structure may be sensed by the sensor assembly 50 by transmitting the electrical signal directionally or radially outward from the transmitting electrode 50a, as indicated by arrows "A" and "A'" in FIG. 5, such that the transmitted electrical signals will contact anatomical structures in the proximity of sensor assembly 50 to elicit a response therefrom that is received by the receiving electrode 50b, as indicated by arrows "B" and "B'" in FIG. 5, and subsequently processed by the processing unit 25. In this manner, the processing unit 25 may determine both the identity of the target anatomical structure, as discussed hereinabove, and the distance between the sensor assembly 50 and the target anatomical structure. In this scenario, the user may be alerted with increased conspicuousness or urgency as the sensor assembly 50 gets closer to the target anatomical structure. For example, the alert generated by audio/visual indicator 22 may vary audibly (e.g., volume, frequency, timing, style, etc.) and/or visually (e.g., frequency, brightness, color, style, etc.) depending on the proximity of the target anatomical structure to the sensor assembly 50. In this manner, as the distance between sensor assembly 50 and a target anatomical structure decreases, the alert generated by the audio/visual indicator 22 may be more conspicuous or more urgent relative to an alert corresponding to a greater distance between sensor assembly 50 and the target anatomical structure to indicate to the user that the sensor electrode 50 is approaching a critical anatomical structure that should be avoided. In some embodiments, output from the generator 20 (e.g., RF energy) to the instrument being utilized in the procedure (e.g., monopolar instrument 2, bipolar forceps 10) may be set by the surgeon to be modified or terminated based on the distance between the sensor assembly 50 and the target anatomical structure. In this instance, output from the generator 20 may be terminated or decreased if the instrument gets too close to a critical anatomical structure (e.g., hepatic artery, common bile duct, etc.) not intended to be treated or contacted by an instrument. The visual output of the sensor assembly 50 (e.g., electrical, thermal, optical, etc.) may be presented on a monitor included on the generator 20 or on another suitable display device in the operating room (e.g., camera monitor).

Figure 6:
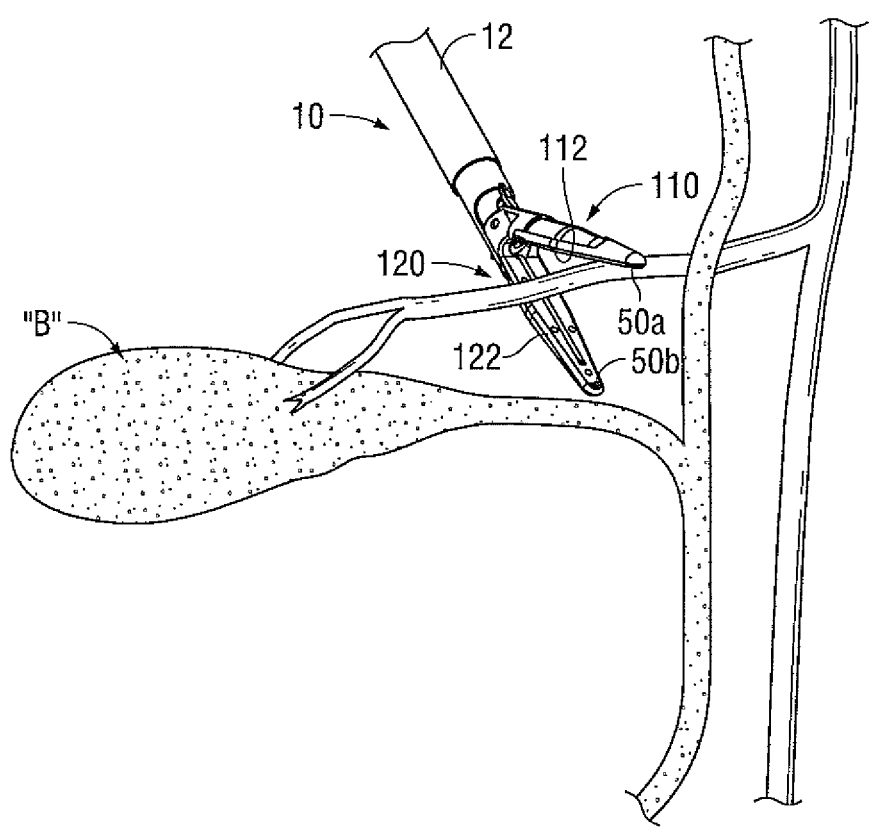
FIG. 6 is a perspective view of a bipolar forceps disposed relative to a gallbladder region of a patient in accordance with an embodiment of the present disclosure.

Referring now to FIG. 6, forceps 10 is shown including transmitting electrode 50a and receiving electrode 50b disposed on a distal portion of jaw members 110 and 120, respectively. In the illustrated embodiment, jaw members 110, 120 are disposed about a target anatomical structure (e.g., cystic artery) and in the open position. In this scenario, either prior to or while grasping the target structure between jaw members 110, 120, electrodes 50a, 50b are utilized in conjunction with processing device 25 to identify the target structure, using methods described hereinabove. For example, transmitting electrode 50a disposed on jaw member 110 may be utilized to transmit an electrical signal to receiving electrode 50b disposed on jaw member 120 via the conductive tissue of the cystic artery to elicit a measurable response from the cystic artery. Depending on the identity of the target structure, forceps 10 may grasp the target structure, if not already grasped, and selectively apply electrosurgical energy thereto or, alternatively, be moved away from the identified structure to avoid injury thereto. For example, the forceps 10 may be moved away from the cystic artery and toward the gallbladder to elicit a measureable response therefrom (as illustrated in FIG. 4B) utilizing the conductive tissue of the gallbladder and/or the conductive content within the gallbladder (e.g., bile), referenced generally as "B".

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for determining proximity of a surgical device relative to an anatomical structure, the method comprising the steps of:
    placing at least one surgical device having a sensor assembly disposed thereon relative to a target anatomical structure, the at least one surgical device including a pair of jaw members movable relative to each other;
    transmitting at least one first electrical signal from the sensor assembly via one of the jaw members through a content of the target anatomical structure to the other jaw member to elicit a measurable response from the content of the target anatomical structure;
    calculating one or more signature properties of the target anatomical structure based on the measureable response;
    comparing values of at least one first measured signature property to at least one second measured signature property; and
    determining the identity of the target anatomical structure and proximity of the at least one surgical device relative to the target anatomical structure based on the comparison between the at least one first measured signature property and the at least one second measured signature property.

2. A method according to claim 1, further comprising the step of modifying an application of electrosurgical energy to the target anatomical structure based on the determining step.

3. A method according to claim 1, wherein the at least one electrical signal of the transmitting step is transmitted from a transmitting electrode of the sensor assembly through the anatomical structure to a receiving electrode of the sensor assembly.

4. A method according to claim 1, wherein the measurable response is based on at least one of tissue of the target anatomical structure and at least one fluid within the target anatomical structure.

5. A method according to claim 4, wherein the at least one fluid is selected from the group consisting of blood, bile, urine, feces, saliva, water, mucus, and digestive enzymes.

6. A method according to claim 1, further comprising the step of delivering a contrast agent through the target anatomical structure to modify the measurable response.

7. A method according to claim 1, wherein the at least one second measured signature property is at least one known signature property of the target anatomical structure.

8. A method according to claim 1, wherein the placing step further comprises the step of grasping the target anatomical structure prior to the transmitting step.

* * * * *